United States Patent [19]

Muller et al.

[11] 4,291,124
[45] Sep. 22, 1981

[54] PROCESS FOR THE ACID HYDROLYSIS OF CARBOHYDRATE POLYMERS AND THE CONTINUOUS FERMENTATION OF THE SUGARS OBTAINED THEREFROM TO PROVIDE ETHANOL

[75] Inventors: Werner C. Muller, Dobbs Ferry, N.Y.; Franklyn D. Miller, Cincinnati, Ohio

[73] Assignee: National Distillers and Chemical Corp., New York, N.Y.

[21] Appl. No.: 129,518

[22] Filed: Mar. 12, 1980

Related U.S. Application Data

[63] Continuation-in-part of Ser. No. 52,038, Jun. 25, 1979, Pat. No. 4,242,455.

[51] Int. Cl.³ .............................................. C12P 7/14
[52] U.S. Cl. .................................... 435/162; 435/813; 435/940; 435/942
[58] Field of Search .............................. 435/162, 813

[56] References Cited

U.S. PATENT DOCUMENTS

| | | | |
|---|---|---|---|
| 2,419,960 | 5/1947 | Legg | 435/162 |
| 2,431,004 | 11/1947 | Wickerham | 435/162 X |
| 3,337,414 | 8/1967 | Wilson | 435/96 |
| 4,009,075 | 2/1977 | Hoge | 435/162 |
| 4,132,595 | 1/1979 | Hebeda | 435/96 |

*Primary Examiner*—Lionel M. Shapiro
*Attorney, Agent, or Firm*—Kenneth D. Tremain

[57] ABSTRACT

A carbohydrate polymer such as starch and/or cellulose is converted to ethanol by a process in which an aqueous slurry of the carbohydrate polymer acid hydrolyzed to provide a sterile fermentable sugar solution is thereafter continuously converted by fermentation to dilute aqueous ethanol ("beer") in a series of agitated fermentations vessels which contain progressively more ethanol and less fermentable suger employing at least two strains of yeast for the fermentation, one of which provides a high rate of ethanol production in a fermentation medium containing a relatively low concentration of ethanol and a relatively high concentration of fermentable sugar and the other of which provides a high rate of ethanol production in a fermentation medium containing a relatively high concentration of ethanol and a relatively low concentration of fermentable sugar.

19 Claims, 3 Drawing Figures

PROCESS FOR THE ACID HYDROLYSIS OF CARBOHYDRATE POLYMERS AND THE CONTINUOUS FERMENTATION OF THE SUGARS OBTAINED THEREFROM TO PROVIDE ETHANOL

CROSS REFERENCE TO RELATED APPLICATIONS

This application is a continuation-in-part of commonly assigned copending U.S. patent application Ser. No. 052,038 filed June 25, 1979, now U.S. Pat. No. 4,242,455 granted Dec. 30, 1980 and is related to commonly assigned copending U.S. patent application Ser. Nos. 043,190, filed May 29, 1979 now U.S. Pat. No. 4,242,454 granted Dec. 30, 1980 and 043,193, filed May 29, 1979, now U.S. Pat. No. 4,243,750 granted Jan. 6, 1981 entitled "Fermentation Process" and "Process for the Hydrolysis of Starch and the continuous Fermentation of the Sugars obtained therefrom to provide Ethanol", respectively, and U.S. patent application Ser. Nos. 052,037, filed June 25, 1979, now abandoned and copending 091,640, filed Nov. 5, 1979, each entitled "Acid Hydrolysis of Carbohydrates Polymers".

BACKGROUND OF THE INVENTION

1. Field of the Invention

This invention relates to processes for hydrolyzing carbohydrate polymers such as starch and cellulose and more particularly, to such processes especially adapted to provide substrate sugars for the fermentation of ethanol.

2. Description of the Prior Art

With the ever-increasing depletion of economically recoverable petroleum reserves, the production of ethanol from vegetative sources as a partial or complete replacement for conventional fossil-based liquid fuels becomes more attractive. In some areas, the economic and technical feasibility of using a 90% unleaded gasoline-10% anhydrous ethanol blend ("gasohol") has shown encouraging results. According to a recent study, gasohol powered automobiles have averaged a 5% reduction in fuel compared to unleaded gasoline powered vehicles and have emitted one-third less carbon monoxide than the latter. In addition to offering promise as a practical and efficient fuel, biomass-derived ethanol in large quantities and at a competitive price has the potential in some areas for replacing certain petroleum-based chemical feedstocks. Thus, for example, ethanol can be catalytically dehydrated to ethylene, one of the most important of all chemical raw materials both in terms of quantity and versatility.

The various operations in processes for obtaining ethanol from such recurring sources as cellulose, cane sugar, amylaceous grains and tubers, e.g., the separation of starch granules from non-carbohydrate plant matter and other extraneous substances, the acid and/or enzymatic hydrolysis of starch and/or cellulose to fermentable sugar (saccharification), the fermentation of sugar to a dilute solution of ethanol ("beer") and the recovery of anhydrous ethanol by distillation, have been modified in numerous ways to achieve improvements in product yield, production rates and so forth. For ethanol to realize its vast potential as a partial or total substitute for petroleum fuels or as a substitute chemical feedstock, it is necessary that the manufacturing process be as efficient in the use of energy and raw materials as possible so as to maximize the energy return for the amount of ethanol produced and enhance the standing of the ethanol as an economically viable replacement for petroleum-based chemicals. To date, however, relatively little concern has been given to the energy requirements for manufacturing ethanol from biomass and consequently, little effort has been made to minimize the thermal expenditure for carrying out any of the discrete operations involved in the manufacture of ethanol from vegetative sources.

The substitution of alcohol for at least a portion of petroleum-based fuels is particularly critical for developing economies where proven domestic petroleum reserves are limited, such as in India and Brazil and these nations have therefore increasingly emphasized the production of alcohol from vegetative sources. The most common such operation employs cane sugar in a fermention-distillation operation which conveniently utilizes the bagasse by-product as a fuel source. Cassava or manioc (*Manihot utilissima Pohl*) as a source of starch has also been considered for conversion into alcohol (see "Brazil's National Alcohol Programme", Jackson, ed (*Process Biochemistry* pp. 1781–1783 (1950); and United Kingdom Pat. No. 1,277,002). However, since manioc lacks the equivalent of sugar cane's bagasse, the fuel for alcohol conversion must come from an external source. Thus, to make manioc root starch or for that matter, any carbohydrate polymer, an economically attractive source of ethanol, it is essential to achieve rapid and high levels of conversion of the carbohydrate polymer to fermentable saccharide and of the fermentable saccharide to ethanol with high levels of thermal efficiency and at low plant investment and operating costs.

Numerous processes for the acid hydrolysis of cellulose and starch to provide fermentable saccharides are known (viz., the acid starch hydrolysis processes described in U.S. Pat. Nos. 2,203,325; 2,210,659; 3,359,763; 2,393,095; 2,395,907; 2,565,404; 2,946,706; 2,954,304; 2,989,425; 3,169,083; 3,200,012; 3,236,687; 3,313,654; 3,446,664; 3,484,287; 3,607,395 and 4,137,654 and, the acid cellulose hydrolysis processes described in U.S. Pat. Nos. 1,096,030; 1,242,030; 1,355,415; 1,428,217; 1,641,771; 1,697,785; 1,806,531; 1,828,982; 1,890,304; 1,919,623; 1,936,190; 1,936,972; 1,969,646; 1,990,097; 2,008,284; 2,086,701; 2,086,963; 2,088,977; 2,108,567; 2,220,846; 2,239,095; 2,284,500; 2,302,022; 2,305,833; 2,356,500; 2,426,677; 2,450,586; 2,474,669; 2,488,981; 2,516,833; 2,681,871; 2,735,792; 2,739,086; 2,752,270; 2,759,856; 2,778,751; 2,801,939; 2,835,611; 2,851,382; 2,900,284; 2,945,777; 2,951,775; 2,959,500; 2,974,067; 3,067,065; 3,212,932; 3,212,933; 3,251,716; 3,479,248; 3,523,911; 3,640,768; 3,787,241; 4,018,620; and 4,029,515).

The acid hydrolysis of manioc root starch with mineral acid preparative to fermentation of the resulting sugar to produce ethanol has been investigated (see "Tapioca as a Source of Alcohol", Krishnamurti, E. G. 1960, *Current Science* 9:346–348). However, the hydrolysis could not be effected without the addition of fresh acid. Moreover, under the conditions employed (heating at 50–60 p.s.i. with 2% sulfuric acid for 4 hours), the hydrolyzed starch solution developed a dark color and a burnt smell which would signal saccharide degradation. Hydrolysis of the starch with lower amounts of sulfuric acids, i.e., 0.5% and 1.0% respectively, under the foregoing conditions failed to provide complete hydrolysis.

Processes for the continuous fermentation of sugars to provide alcohol are well known (viz., U.S. Pat. Nos. 2,155,134; 2,371,208; 2,967,107; 3,015,612; 3,078,166; 3,093,548; 3,177,005; 3,201,328; 3,207,605; 3,207,606; 3,219,319; 3,234,026; 3,413,124; 3,528,887; 3,575,813; 3,591,454; 3,705,841; 3,737,323; and 3,940,492; "Process Design and Economic Studies of Alternative Fermentation Methods for the Production of Ethanol", Cysewski, et al. *Biotechnology and Bioengineering,* Vol. xx, pp. 1421–1444 (1978)). In a typical continuous fermentation process, a stream of sterile sugar liquor and a quantity of yeast cells are introduced into the first of a battery of fermentation vessels wherein initial fermentation takes place, generally under conditions favoring rapid cell growth. The partial fermentate admixed with yeast cells is continuously withdrawn from the first fermentation vessel wherein fermentation is carried out under conditions favoring the rapid conversion of sugar to ethanol. The yeast in the last fermentation vessel can be recovered by suitable means, e.g., centrifugation or settlement, and recycled. In such a system, the ability of the fermentation organism to produce ethanol is affected by the ethanol and sugar concentrations. As a rule, a yeast which gives high conversion rates of sugar to ethanol in a low-ethanol, high-sugar fermentation medium will only sluggishly produce ethanol under the opposite conditions, i.e., at high-ethanol level, low-sugar concentrations.

Accordingly, there has heretofore existed a need for a process for the acid hydrolysis of carbohydrate polymers from cellulose and/or starch at rapid and high levels of conversion without any significant degradation of the resulting saccharide and at only a modest expenditure of thermal energy and of utilizing the saccharide in a thermally efficient, rapid continuous fermentation process to provide industrial ethanol at competitive prices.

SUMMARY OF THE INVENTION

In accordance with the present invention, an acidified aqueous slurry of carbohydrate polymer particles such as starch granules and/or cellulose chips, fibers, etc., is mixed with steam under pressure and conveyed through a conduit at substantially steady state temperature and pressure for a period sufficient to accomplish at least about 60% weight conversion, and preferably at least about 80% weight conversion, of the carbohydrate polymer to fermentable hydrolysate but without appreciable conversion of carbohydrate polymer to non-fermentable products. The pressurized acidified carbohydrate slurry is then passed through an expansion valve or critical flow orifice resulting in an abrupt reduction of pressure on the product hydrolysate and a cessation of, or considerable reduction in, further hydrolyzing activity. This abrupt reduction in pressure serves to prevent or diminish the likelihood of any further reaction tending to produce unfermentable reversion or decomposition products and thus maximizes the yield of useful hydrolysate, i.e., fermentable sugar. Among the sources of carbohydrate polymers which can be employed herein are cellulosic materials such as wood, wood chips, sawdust, bark, and plant fiber, the cellular tissue of root crops such as manioc, potatoes, yams, turnips, beets, carrots and the like, and starch from grains such as corn, rice, wheat, milo, and their mixtures. The carbohydrate polymer slurry can contain from about 20 to about 50 weight percent dry substance (D.S.) or more, and preferably contains from about 30 to about 40 weight percent D.S. to facilitate pumping. The slurry can also contain other components of the source material such as water soluble proteins, fats, sugars and minerals and/or water insoluble materials such as minute amounts of gravel, etc. While the carbohydrate polymer can be extracted from the source material employing any of the known and conventional procedures, it is especially advantageous in the case of starch as the starting material herein to use either of the starch recovery processes disclosed in commonly assigned copending U.S. patent applications Ser. Nos. 043,192, filed May 29, 1979, now U.S. Pat. No. 4,247,638, and Ser. No. 069,950, filed Aug. 27, 1979, now U.S. Pat. No. 4,255,518.

Acidification of the carbohydrate polymer slurry can be accomplished with any strong inorganic acid, i.e., an acid having a pKa value of at least about 2.0 or less. Examples of strong inorganic acids which can be used include nitric acid, sulfuric acid, hydrochloric acid and phosphoric acid. Neutralization of the acid following conversion of the carbohydrate polymer to fermentable sugar can be accomplished with any suitable base. However, when the product sugar is to be used as a substrate for the production of ethanol by microbial fermentation, it is preferred to employ ammonia or aqueous ammonia as the neutralizing base since the resulting ammonium salt will be available to satisfy nutrient requirements of the fermenting organisms.

Following conversion of the carbohydrate polymer to fermentable sugar, the latter is introduced, with or without any partial hydrolysate which may be present therein having been previously further saccharified, into a series of fermentation vessels wherein fermentation of sugar to ethanol by yeast and the saccharification of partial hydrolysate, if present, to fermented sugar takes place. The ethanol content of the fermentation medium in each fermentation vessel is progressively increased as the sugar content of the fermentation medium is consumed, there being at least two strains of yeast selected for the fermentation, one of which provides a high rate of ethanol production in a fermentation medium containing a relatively low concentration of ethanol and a relatively high concentration of fermentable sugar and the other of which provides a high rate of ethanol production in a fermentation medium containing a relatively high concentration of ethanol and a low concentration of fermentable sugar. Employing two or more organisms which maintain high rates of ethanol production in the presence of different concentrations of ethanol and fermentable sugar provides a faster, more efficient fermentation than that attainable employing a single strain of yeast in each fermentation vessel as is the current practice. As such, the fermentation process of this invention is particularly well suited for the production of ethanol which is price competitive with ethanol produced from non-vegetative sources.

The process herein also contemplates the adjustment of temperature and/or pH in each fermentation vessel as required to maintain optimum fermentation activity therein. To conserve raw materials and direct yeast metabolic activity to the production of ethanol rather than cell growth and propagation, a portion of the yeast is continuously recycled and additional fresh yeast is added only as is necessary to replace dead cells. The aqueous ethanol or "beer" containing as much as about 12 weight percent ethanol which is obtained by the foregoing process can be concentrated employing any of the known and conventional techniques and is advantageously concentrated by the anhydrous distillation process disclosed in commonly assigned copending U.S. patent application Ser. No. 043,189, filed May 29, 1979. The stillage effluent obtained from the rectifying column employed in the aforesaid distillation process contains soluble proteins and amino acids of the original beer feed and provides an excellent source of nutrient for yeast employed in the fermentation process herein.

The terms "fermentable sugar" and "fermentable hydrolysate" as used herein are to be understood as referring to a single fermentable sugar such as glucose (dextrose), fructose, maltose or sucrose but more commonly will be applicable to these and similar fermentable saccharides in admixture.

BRIEF DESCRIPTION OF THE DRAWINGS

In the accompanying drawings.

DESCRIPTION OF THE PREFERRED EMBODIMENTS

Figure 1A:
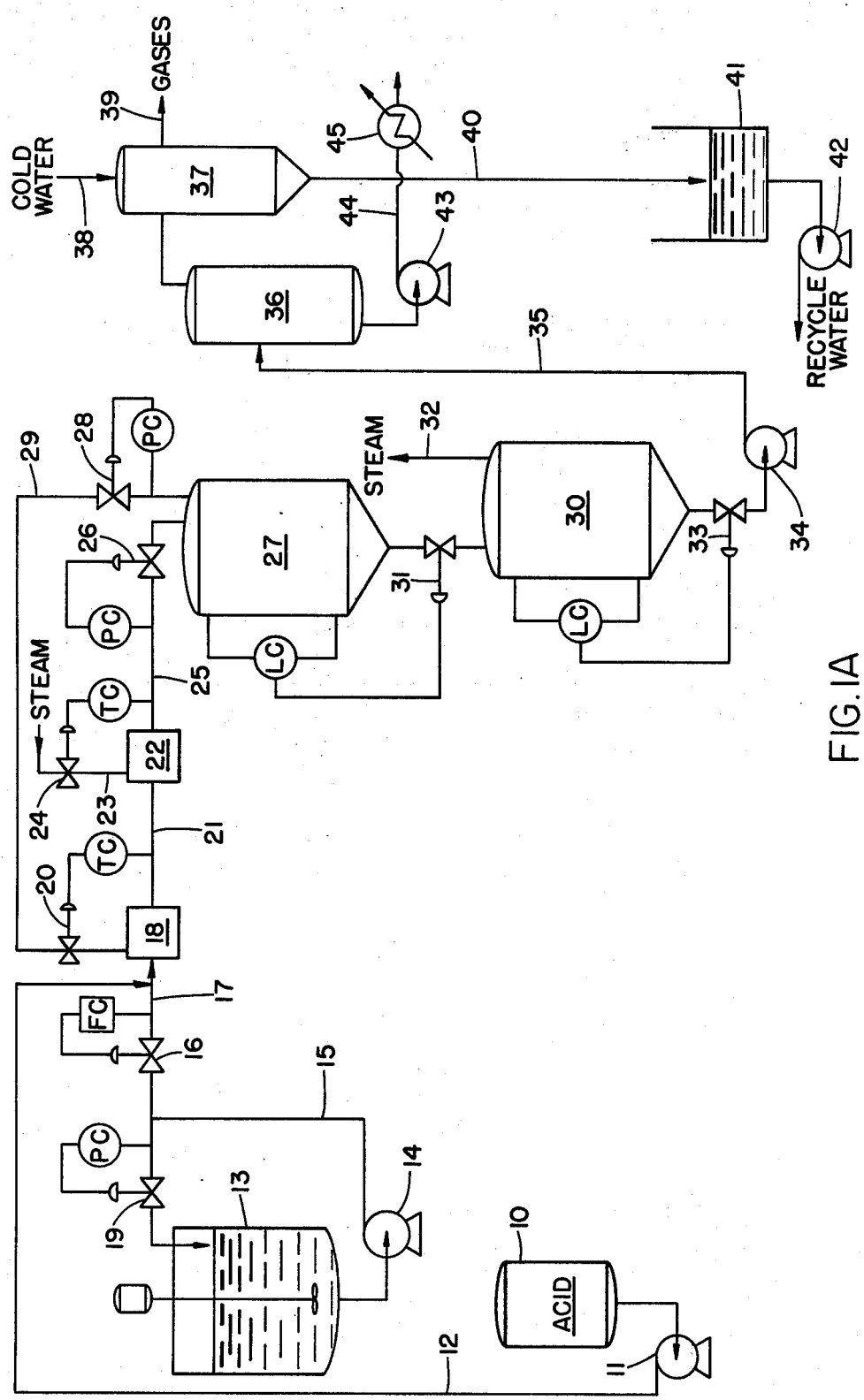
FIGS. 1A and 1B are diagrammatic flow sheets illustrating separate embodiments of the acid hydrolysis stage of the invention and FIG. 1C is a diagrammatic flow sheet illustrating the fermentation stage of the invention.

Referring to FIG. 1A, a hydrolyzing effective amount of a strong acid such as hydrochloric acid in vessel 10 is transferred by pump 11 through line 12, the acid being combined with pressurized manioc root starch or other starch passing through line 17 to optional steam jet mixer 18. The manioc root starch may contain the cellulosic fiber component of the root and will generally contain from about 10 to about 50 D.S., and preferably, from about 30 to 40 D.S. In lieu of starch, the carbohydrate polymer to undergo hydrolysis in accordance with this invention can be entirely that of cellulose. The starch slurry is taken from agitated vessel 13 and conveyed by pressurizing pump 14 through line 15. Flow control valve 16 maintains a relatively constant pressure of slurry passing through line 17 to steam jet mixer 18 while pressure control valve 19 relieves excess pressure on line 15 and recycles a portion of the slurry to vessel 13 as may from time to time be necessary. The pressure imparted to the slurry by pump 11 can vary over fairly wide limits. Pressures on the order of from about 100 to about 1,000 psig and advantageously, from about 600 to about 900 psig, provide good results. The amount of strong acid combined with slurry passing through line 17 will ordinarily be sufficient to provide substantially complete hydrolysis of the polymer to fermentable sugar. Alternatively, however, the total amount of acid required for complete hydrolysis can be divided into two or more portions with one portion being combined with the slurry prior to passage of the slurry through optional or auxiliary steam jet mixer 18, another portion being combined with the slurry prior to passage of the slurry through main steam jet mixer 22, and the remaining portion (s) of acid, if any, being introduced elsewhere in the system, advantageously in expansion vessel 27 and/or expansion vessel 28, to provide complete hydrolysis. The use of optional steam jet mixer 18 equipped with temperature control valve 20 is operationally and economically advantageous herein in that it utilizes the low pressure steam, e.g., up to 50 psig, issuing from vessel 27 to effect partial hydrolysis of the starch and to make the starch even more accessible to hydrolysis after being mixed with relatively high pressure steam in main steam jet mixer 22. Following passage through optional steam jet mixer 18, the starch slurry enters line 21 wherein some hydrolysis takes place. The partially hydrolyzed starch then enters main steam jet mixer 22 where it is combined with steam supplied through line 23 with steam pressure in this line being maintained by temperature control valve 24. The pressure of the steam introduced into main steam jet mixer 22 is substantially higher than the pressure in line 25 to provide a high volumetric flow rate therethrough. The amount of steam delivered to main steam jet mixer 22 should be sufficient to provide a slurry temperature in line 25 which, in the case of starch, can be in the range of from about 140° C. to about 200° C., and preferably, from about 160° C. to about 200° C., and in the case of cellulose, can be in the range of from about 180° C. to about 290° C., and preferably, from about 220° C. to about 270° C. Steady state temperature and pressure are maintained in line 25 through temperature control valve 24 and pressure control valve 26. In place of pressure control valve 26, line 25 may be provided with a critical flow orifice to maintain a predetermined level of pressure in the line. Hydrolysis of the starch substantially to completion takes place rapidly in line 25, the retention time of the carbohydrate slurry therein being preferably kept as brief as possible (consistent with obtaining good sugar yields) in order to minimize breakdown of the sugar hydrolysate and/or other undesirable side reactions. In general, the retention time of the slurry in line 25 can vary from about 0.1 to about 300 seconds, and advantageously from about 0.5 to about 10 seconds. Such retention times will provide conversion levels of carbohydrate polymer to fermentable hydrolysate of at least about 60% by weight and preferably at least about 80% by weight. The length of line 25, i.e., the distance from main steam jet mixer 22 to pressure control valve 26, for a given retention time is given by the relationship $$L = L \times R/A$$

wherein

L = length of line 25 in feet;
T = retention time of the carbohydrate slurry in line 25 in seconds;
R = volumetric flow rate of the carbohydrate slurry in line 25 in cubic feet per second; and,
A = internal area of line 25 in square feet.

Passing through pressure control valve 26, the hydrolyzed starch slurry undergoes a sudden pressure reduction in expansion vessel 27 with pressure control valve 28 regulating the amount of steam released therefrom. The pressure in vessel 27 can be maintained on the order of from about 0 to about 50 psig, the vented steam, if any, being conveyed through line 29 either to the atmosphere or advantageously, to optional steam jet mixer 18 as aforedescribed. In this way, thermal values which might otherwise be lost are recovered and put to good use in pre-heating and pre-hydrolyzing the carbohydrate polymer slurry. The entire pressure of the product hydrolysate in vessel 27 in excess of atmospheric pressure can be relieved therefrom or, as shown, the pressure can be reduced step-wise in one or more additional expansion vessels such as vessel 30. Partially pressurized hydrolysate from expansion vessel 27 is admitted to expansion vessel 30 through level control valve 31. Residual superatmospheric pressure steam is released from expansion vessel 30 through line 32. The fully depressurized hydrolysate thereafter passes through level control valve 33 and is driven by pump 34 through line 35 to vacuum cooling chamber 36. Vacuum for chamber 36 is produced in cold water spray vessel 37 supplied with cold water through line 38, the non-condensible gases being vented to the atmosphere through line 39 and the condensate passing through line 40 to storage vessel 41 being recycled to process by pump 42. The vacuum-cooled hydrolysate (sugar liquor) from chamber 36 at a temperature of from about 60° C. to about 80° C. is delivered by pump 43 through line 44 to heat exchanger 45 to further cool the hydrolysate to a temperature suitable for fermentation, e.g., within the range of from about 30° C. to about 35° C.; and thereafter the hydrolysate is introduced to the first of a series of fermentation vessels as diagrammatically illustrated in FIG. 1C.

Figure 1B:
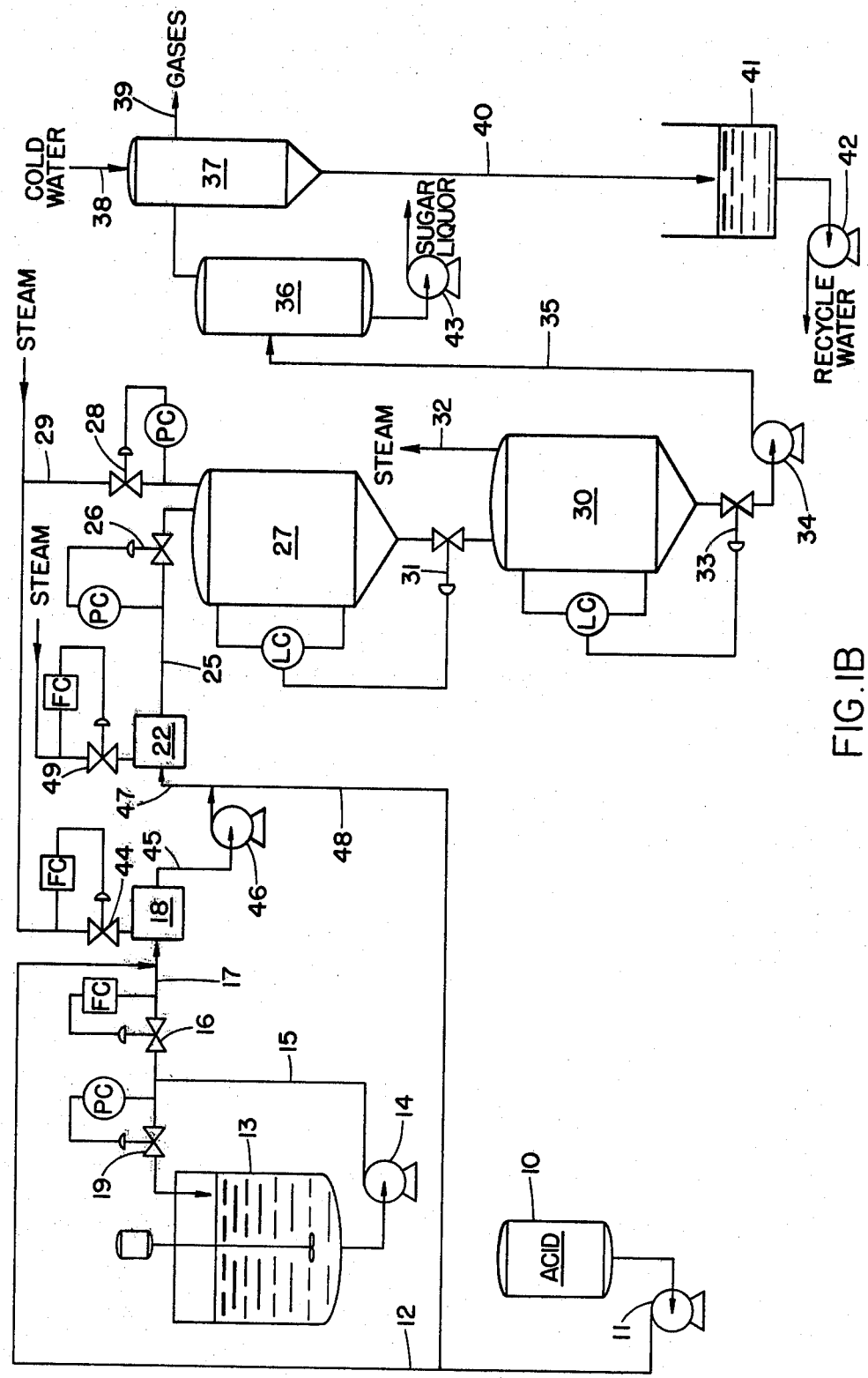

Referring to FIG. 1B, the flow diagram and reference numerals employed therewith are identical to those on FIG. 1A with the exception of certain elements associated with optional steam jet mixer 18 and main steam jet mixer 22 as hereinafter described. As the aqueous acidified carbohydrate polymer slurry enters optional steam jet mixer 18, it is combined with steam passing from line 29 through flow control regulating valve 44 to provide a turbulent, high velocity dual phase flow, liquid and steam, through line 45. Back pressure in line 45 is advantageously maintained by a pressure control valve. The temperature in this first optional reaction zone is advantageously maintained within the range of from about 90° C. to about 150° C. or higher at saturation pressure to maintain the dual phase flow. Providing such a dual phase flow results in several operational advantages. Since the vapor component of the flow results in the breaking up of the carbohydrate component into tiny droplets, the stream will possess a lower density than it would possess in a single phase flow. This lower density permits higher flow velocities and shorter time of contact of the carbohydrate with hydrolyzing acid. Due to the highly turbulent, high velocity flow imparted to the acidified slurry by the flow control regulated steam, the carbohydrate quickly liquifies to provide a readily pumpable slurry of partial hydrolysate which is thereafter subjected to further hydrolysis to fermentable sugar. If desired, the pressure in line 45 can be operated above the saturation pressure to provide a single phase, liquid flow therethrough. The liquified carbohydrate passing through line 45 is then forced by pump 46 through line 47 where it may be combined with an additional quantity of acid through line 48. The further acidified liquid starch enters main steam jet mixer 22 where it is combined with high pressure steam regulated by flow control regulating valve 49 and then passes through line 25 where further hydrolysis takes place. The temperature in line 25 regardless of whether there has been a pre-treatment of the slurry with low pressure steam in optional steam jet mixer 18 is preferably maintained in the range of from about 140° C. to about 215° C. or higher at saturation pressure to provide dual phase flow or if desired, above saturation pressure to maintain a single phase, liquid flow.

If prior to being used in fermentation, storage of the hydrolysate for relatively long periods of time is contemplated, the hydrolysate should be maintained at a temperature of at least about 60° C. to inhibit any repolymerization of partial hydrolysates contained therein. Since hydrolysate from chamber 36 will generally be at this minimum level of temperature, it is convenient to convey the hydrolysate by pump 43 directly to a storage vessel without subjecting the hydrolysate to any prior cooling. If a carbohydrate polymer slurry is employed in the foregoing process which contains insoluble matter, such matter should be separated from the product sugar prior to the use of the latter in fermentation in order to prevent the accumulation of such matter in the fermentation vessel(s). The separation can be readily accomplished employing any of the known and conventional techniques such as filtration, centrifugation, etc.

Figure 1C:
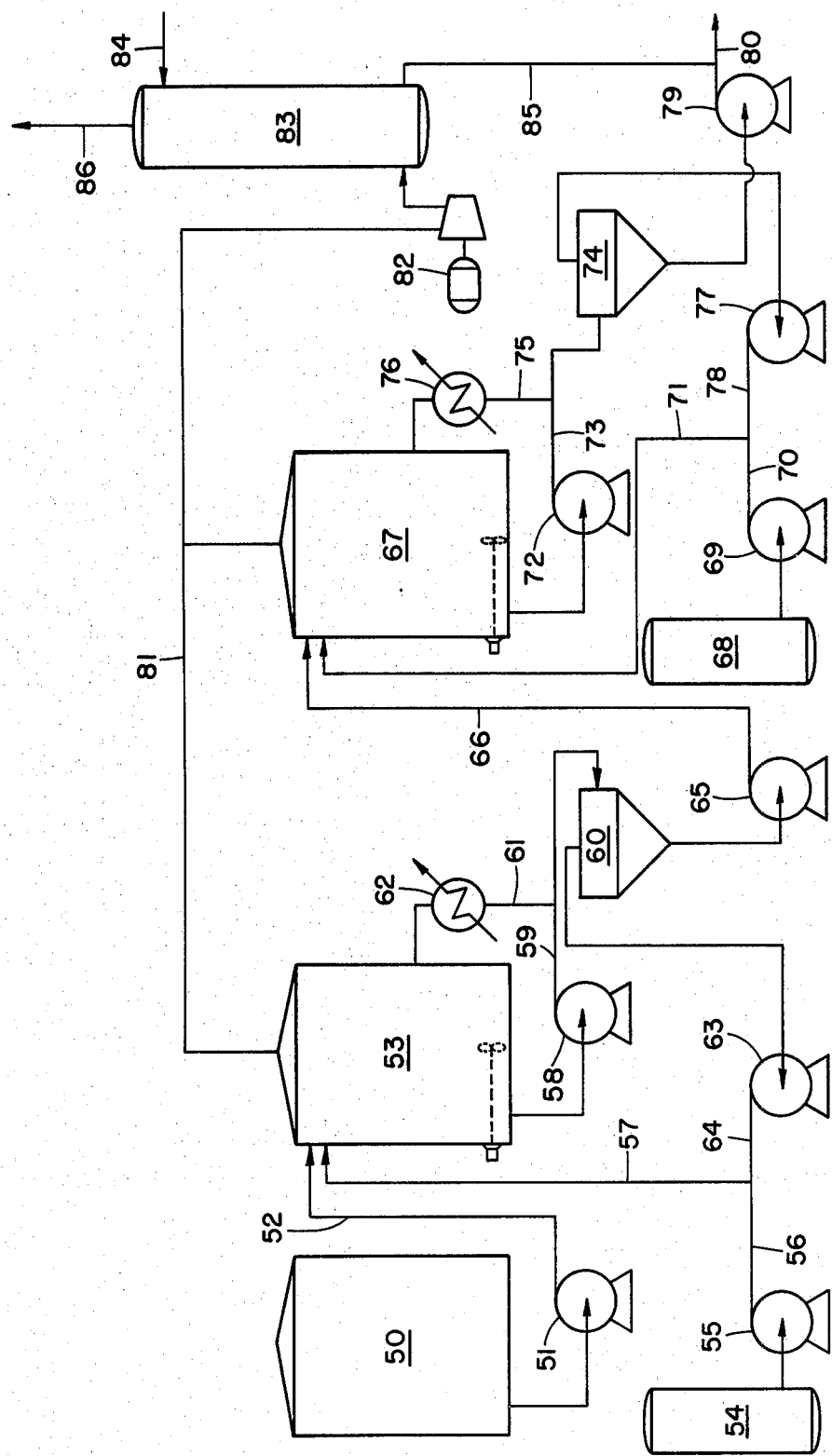

Referring to FIG. 1C, the sterile aqueous solution of fermentable hydrolysate (sugar) resulting from the hydrolysis stage of FIG. 1A or 1B, containing from about 10 to about 40 weight percent sugar, and preferably from about 15 to about 25 weight percent sugar, is taken from storage vessel 50 and is delivered by pump 51 through line 52 to a first temperature regulated, agitated fermentation vessel 53 provided with pH control and means for introducing nutrients and the small amounts of oxygen conventionally employed for maintaining proper yeast metabolism during fermentation.

Prior to introduction into the first fermentation vessel, the pH of the hydrolysate is generally adjusted with base to provide a pH conducive to rapid levels of fermentation, e.g., from about 3.5 to about 5.5 and preferably from about 4.0 to about 4.6. Liquid or aqueous ammonia is especially preferred for adjusting the pH of the hydrolysate as the resulting ammonium nitrate, sulfate, chloride and/or phosphate salt is retained in the hydrolysate and is available to satisfy a nutritional need of the yeast employed in the fermentation phase of the process. The addition of ammonia (or other base) to the hydrolysate to effect neutralization of the latter can be made at any convenient point in the hydrolysis system, e.g., in vessel 30 or 36.

In the event the sugar solution contains more than 20 weight percent sugar, it is preferably to dilute the solution to about this level of sugar, advantageously with the nitrogen-rich stillage obtained from an ethanol distillation unit such as described in the aforesaid Ser. No. 043,189. The use of stillage when available possesses the two-fold advantage of recycling nitrogen to the fermentation system which would otherwise be lost upon concentration of the ethanol during distillation, and reducing process water consumption by avoiding water build-up in the still bottoms. The hydrolysate may, in addition to sugar, contain significant amounts of partial starch hydrolysates (e.g., up to about 40 weight percent of the total carbohydrate present) which can be saccharified to fermentable sugar under the influence of the saccharifying enzyme produced by the fermenting yeast and/or added saccharifying enzyme. A pumpable slurry of ethanol-producing yeast organisms free of contaminating organisms is conveyed from yeast storage tank 54 by pump 55 through line 56 and 57 into fermentation vessel 53. The yeast selected for introduction in fermentation vessel 53 is one which provides high rates of ethanol production in the presence of relatively low concentrations of ethanol and relatively high concentrations of fermentable sugar. Yeasts which will perform in this manner can be selected employing known microbiological techniques. Thus, for example, several strains of yeast can be introduced into a laboratory or large scale fermentation vessel (e.g., a chemostat) in which initial ethanol, sugar and nutrient concentrations are noted and predetermined levels of temperature and pH are accurately maintained so as to simulate the conditions present in a commercial fermentation unit. As the different strains of yeast compete with one another for survival over a prolonged period which can be several weeks or even months, only one or a few strains will have survived, the surviving organisms being optimal producers of ethanol under the conditions selected for the operation of the fermentation unit. Using the same procedure, the mutation of a single yeast organism to provide an optimal ethanol producer under the fermentation conditions selected can be induced. The foregoing screening procedure can also be used to evaluate and isolate selected strains of yeast produced by techniques of induced mutation, e.g., those employing ultraviolet radiation, gamma rays, etc., to accelerate the incidence of mutation. Other useful techniques for obtaining different strains of yeast for evaluation as ethanol producers under predetermined fermentation conditions include cross breeding of two different strains to yield a third and genetic engineering in which genetic materials from two different strains are recombined to form a completely new genetic "blueprint". A yeast which has been found to provide especially good rates of ethanol production at relatively low concentrations of ethanol and relatively high concentrations of fermentable sugar is *Saccharomyces bayanus*. The yeast in fermentation vessels 53 and 67 can be present at a level of from about 2 to about 8 weight percent of the fermentation medium (based on dry weight of yeast) and preferably is present at from about 3 to about 6 weight percent. Once continuous fermentation has started and a steady state has been achieved, there will be no need to add more yeast other than those amounts necessary to make up for cells which die. The temperature of each fermentation vessels is advantageously regulated at a level which favors maximum ethanol production, i.e., generally from about 68° F. to about 104° F. and preferably from about 86° F. to about 99° F. The pH of each fermentation vessel is similarly regulated and can range from about 3.5 to about 5.5 and preferably from about 4.0 to 4.6. Dilute ethanol produced in fermentation vessel 53 containing a portion of the yeast cells therein is conveyed by pump 58 through line 59 to yeast separator/recovery unit 60 which separates substantially all of the yeast cells from the aqueous ethanol stream. Unit 60 can be a micro-filtration device, centrifuge, etc. Since fermentation is exothermic, a portion of the fermentation medium passing through line 59 is diverted through line 61 into cooler 62 and returned to fermentation vessel 53. The yeast cells recovered in unit 60 are conveyed as a pumpable slurry or "cream" containing from about 10 to about 50 weight percent dry yeast and preferably from about 20 to about 40 weight percent dry yeast by pump 63 through lines 64 and 57 into fermentation vessel 53. The ethanol-containing fermentation medium thus freed of yeast cells is delivered by pump 65 through line 66 into fermentation vessel 67 which is essentially similar to fermentation vessel 53. A pumpable slurry of ethanol-producing yeast organisms essentially free of contaminating organisms is conveyed from yeast storage tank 68 by pump 69 through line 70 and 71 into fermentation vessel 67. The yeast selected for introduction in fermentation vessel 67 is one which provides high rates of ethanol production in the presence of relatively high concentrations of ethanol and relatively low concentrations of fermentable sugar. Strains of yeast satisfying these requirements can be isolated in the manner described above. A yeast which has been found to provide especially good rates of ethanol production at relatively high concentrations of ethanol and relatively low concentrations of fermentable sugar is *Saccharomyces cerevisiae* (Distillers Active Dry Yeast from Red Star Yeast). The dilute aqueous ethanol (approximately 10 to 12 weight percent ethanol) containing yeast cells is withdrawn from fermentation vessel 67 and conveyed by pump 72 through line 73 to yeast separator/recovery unit 74. A portion of the fermentation medium passing through line 73 is diverted through line 75 into cooler 76 and returned to fermentation vessel 67. The yeast cells recovered in unit 74 are conveyed as a pumpable slurry (similar in fluid characteristics to the yeast slurry recovered from unit 60) by pump 77 through lines 78 and 71 to fermentation vessel 67. The cell-free ethanol solution from yeast separator/recovery unit 74 is delivered by pump 79 through line 80 directly to an ethanol concentration unit, e.g., anhydrous distillation apparatus, and/or to a storage facility. It is also within the scope of this invention to employ both types of yeast herein in each fermentation vessel with only one yeast separator/recovery unit (receiving the fermentation medium from the last fermentation vessel in the series) being provided. Metabolically evolved carbon dioxide gas containing ethanol is conveyed from each of fermentation vessels 53 and 67 through common line 81 and by means of blower 82 is introduced into the bottom of ethanol absorption unit 83. Water at ambient temperature entering the top of the absorption unit through line 84 and flowing downwardly, absorbs substantially all of the ethanol vapor rising through the unit. The aqueous solution of ethanol withdrawn from the base of ethanol absorption unit 83 through line 85 is conveyed to line 80 where it is combined with the bulk of the flow from the last fermenter. Vent gases are discharged from ethanol absorption unit 83 through atmospheric vent line 86.

What is claimed is:

1. A process for the acid hydrolysis of carbohydrate polymer and the continuous fermentation of the fermentable sugars therefrom to provide ethanol which comprises:
   (a) substantially uniformly mixing a pressurized acidified aqueous slurry of carbohydrate polymer particles with relatively high pressure stream;
   (b) passing the acidified carbohydrate polymer slurry through a conduit under substantially steady state temperature and pressure for a period sufficient to convert at least about 60% by weight of the carbohydrate polymer to fermentable sugar but without appreciable conversion of carbohydrate polymer to non-fermentable products;
   (c) reducing the pressure of the hydrolyzed carbohydrate polymer slurry to a level at which undesirable reactions of the fermentable sugar present in solution therein cannot readily occur; and
   (d) continuously fermenting the fermentable sugar, previously adjusted to a pH suitable for carrying out fermentation, with or without partial hydrolysate therein having been previously further saccharified, in a series of fermentation vessels in which the ethanol content of the fermentation medium is progressively increased in each fermentation vessel as the fermentable sugar is consumed therein, the fermentation employing at least two different strains of ethanol-producing yeast, one of which provides a high rate of ethanol production in a fermentation medium containing a relatively low concentration of ethanol and a relatively high concentration of sugar and the other of which provides a high rate of ethanol production in a fermentation medium containing a relatively high concentration of ethanol and a relatively low concentration of fermentable sugar.

2. The process of claim 1 wherein the carbohydrate polymer is a cellulosic material.

3. The process of claim 1 wherein the carbohydrate polymer is an amylaceous material.

4. The process of claim 4 wherein the amylaceous material is manioc root starch.

5. The process of claim 4 wherein the amylaceous material is corn starch.

6. The process of claim 1 wherein nitric acid, sulfuric acid, hydrochloric acid or phosphoric acid is added to the aqueous carbohydrate polymer slurry for the acidification thereof.

7. The process of claim 1 wherein the pH of the fermentable sugar solution is adjusted with ammonia or aqueous ammonia prior to fermentation step (d).

8. The process of claim 1 wherein the pH of the fermentable sugar solution is adjusted to within the range of from about 3.5 to about 5.5 prior to fermentation step (d).

9. The process of claim 8 wherein the pH of the fermentable sugar solution is adjusted to within the range of from about 4.0 to about 4.6 prior to fermentation step (d).

10. The process of claim 1 wherein the pressure of the hydrolyzed polymer slurry is reduced stepwise.

11. The process of claim 1 wherein prior to mixture with high pressure steam, the pressurized carbohydrate polymer slurry is substantially uniformly mixed with relatively low pressure steam.

12. The process of claim 11 wherein the low pressure steam is recovered during the reduction of the pressure on the hydrolyzed carbohydrate slurry.

13. The process of claim 1, wherein flow of carbohydrate slurry through the conduit is in two phases.

14. The process of claim 1 wherein the aqueous solution of fermentable sugar contains partial starch hydrolysate in an amount of up to about 40 weight percent of the total carbohydrate present, the partial starch hydrolysates undergoing saccharification to fermentable sugar in one or more fermentation vessels in the series under the influence of saccharifying enzyme produced by the yeast and/or added saccharifying enzyme.

15. The process of claim 1 wherein the strain of yeast which provides a high rate of ethanol production in a fermentation medium containing a relatively low concentration of ethanol and a relatively high concentration of sugar is *Saccharomyces bayanus*.

16. The process of claim 1 wherein the strain of yeast which provides a high rate of ethanol production in a fermentation medium containing a relatively high concentration of ethanol and a relatively low concentration of sugar is *Saccharomyces cerevisiae*.

17. The process of claim 1 wherein each different strain of yeast is separately employed in a fermentation vessel and is separately recovered therefrom and recycled thereto.

18. The process of claim 1 wherein the different strains of yeast are used together in each fermentation vessel and are separated from the last fermentation vessel in the series and recycled to the first fermentation vessel in the series.

19. The process of claim 1 wherein ethanol contained in the carbon dioxide gas evolved during fermentation is recovered.

* * * * *